United States Patent
Fong de los Santos et al.

(10) Patent No.: US 11,504,548 B2
(45) Date of Patent: Nov. 22, 2022

(54) SYSTEMS AND METHODS FOR QUALITY CONTROL IN IMAGE-GUIDED RADIOTHERAPY

(71) Applicant: Mayo Foundation for Medical Education and Research, Rochester, MN (US)

(72) Inventors: Luis E. Fong de los Santos, Rochester, MN (US); Michael P. Grams, Rochester, MN (US); Satomi Shiraishi, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 16/530,039

(22) Filed: Aug. 2, 2019

(65) Prior Publication Data

US 2020/0038684 A1  Feb. 6, 2020

Related U.S. Application Data

(60) Provisional application No. 62/713,683, filed on Aug. 2, 2018.

(51) Int. Cl.
*A61N 5/10* (2006.01)
*G06T 7/246* (2017.01)

(52) U.S. Cl.
CPC ......... *A61N 5/1039* (2013.01); *A61N 5/1031* (2013.01); *A61N 5/1049* (2013.01);
(Continued)

(58) Field of Classification Search
CPC .. A61N 5/1039; A61N 5/1031; A61N 5/1049; A61N 5/1067; A61N 5/1075;
(Continued)

(56) References Cited

U.S. PATENT DOCUMENTS

| 5,548,326 A | 8/1996 | Michael |
| 7,894,649 B2 | 2/2011 | Fu |

(Continued)

FOREIGN PATENT DOCUMENTS

| CN | 101489477 B | * | 8/2011 | ........... A61N 5/1037 |
| CN | 103785112 A | * | 5/2014 | ............... G06K 9/68 |
| WO | WO-2018090091 A1 | * | 5/2018 | ............. A61B 6/032 |

OTHER PUBLICATIONS

Breen SL, et al. Statistical process control for IMRT dosimetric verification. Med Phys. 2008;35:4417-4425.
(Continued)

*Primary Examiner* — Matthew C Bella
*Assistant Examiner* — Kathleen M Broughton
(74) *Attorney, Agent, or Firm* — Quarles & Brady LLP

(57) ABSTRACT

Systems and methods for quality control in image-guided radiotherapy are provided. In some aspects, a method includes acquiring treatment images from a patient using an imaging system, and performing a registration using the treatment images and simulation images acquired during a simulation process. The method also includes computing at least one similarity metric based on the registration performed, and determining a conformance of the at least one similarity metric to predetermined limits. The method further includes generating a report indicative of the conformance.

34 Claims, 10 Drawing Sheets
(5 of 10 Drawing Sheet(s) Filed in Color)

(52) U.S. Cl.
CPC ............ *A61N 5/1067* (2013.01); *G06T 7/248* (2017.01); *A61N 2005/1062* (2013.01); *G06T 2207/10124* (2013.01)

(58) Field of Classification Search
CPC ............ A61N 2005/1062; G06T 7/248; G06T 2207/10124
See application file for complete search history.

(56) References Cited

U.S. PATENT DOCUMENTS

| | | | | |
|---|---|---|---|---|
| 8,559,596 | B2 * | 10/2013 | Thomson | A61B 6/4071 378/65 |
| 9,240,046 | B2 | 1/2016 | Carrell | |
| 9,248,316 | B2 * | 2/2016 | Lachaine | A61B 8/483 |
| 9,764,162 | B1 * | 9/2017 | Willcut | G06T 7/0014 |
| 2012/0109608 | A1 * | 5/2012 | Core | A61N 5/1067 703/6 |
| 2018/0056091 | A1 * | 3/2018 | Jordan | A61N 5/1037 |

OTHER PUBLICATIONS

Brouwer, Charlotte L., et al. "Identifying patients who may benefit from adaptive radiotherapy: Does the literature on anatomic and dosimetric changes in head and neck organs at risk during radiotherapy provide information to help?." Radiotherapy and Oncology 115.3 (2015): 285-294.

Ezzell, Gary, et al. "Common error pathways seen in the RO-ILS data that demonstrate opportunities for improving treatment safety." Practical radiation oncology 8.2 (2018): 123-132.

Gerard K, et al. A comprehensive analysis of the IMRT dose delivery process using statistical process control (SPC). Med Phys. 2009;36:1275-1285.

Goyal S, Kataria T. Image guidance in radiation therapy: techniques and applications. Radiol Res Pract. 2014;2014:1-10.

Graff P, et al. Does IGRTensure target dose coverage of head and neck IMRT patients? Radiother Oncol. 2012;104:83-90.

Graff P, et al. The residual setup errors of different IGRT alignment procedures for head and neck IMRT and the resulting dosimetric impact. Int J Radiat Oncol Biol Phys. 2013;86:170-176.

Grams MP, et al. Analysis of automatic match results for cone-beam computed tomography localization of conventionally fractionated lung tumors. Pract Radiat Oncol. 2014;4:35-42.

Jaffray DA, et al. Safety considerations for IGRT: executive summary. Pract Radiat Oncol. 2013;3:167-170.

Jaffray DA. Image-guided radiotherapy: from current concept to future perspectives. Nat Rev Clin Oncol. 2012;9:688-699.

Nabavizadeh, Nima, et al. "Image guided radiation therapy (IGRT) practice patterns and IGRT's impact on workflow and treatment planning: results from a National Survey of American Society for Radiation Oncology members." International Journal of Radiation Oncology* Biology* Physics 94.4 (2016): 850-857.

Pawlicki T, et al. Quality in radiation oncology. Med Phys. 2007;34:1529-1534.

Pawlicki T, et al. Statistical process control for radiotherapy quality assurance. Med Phys. 2005;32:2777-2786.

Pawlicki T, et al. The systematic application of quality measures and process control in clinical radiation oncology. Semin Radiat Oncol. 2012;22:70-76.

Penney, GP. et al. "A Comparison of Similarity Measures for Use in 2-D-3-D Medical Image Registration," IEEE Transactions on Medical Imaging, vol. 17, No. 4, Aug. 1998, pp. 586-595.

Razlighi QR Spatial Mutual Information as Similarity Measure for 3-D Brain Image Registration, IEEE J. Transl. Eng. Health Med. 2:1800308, 2014.

Shiraishi, S. "Statistical Process Control to Assess the Quality of Image-Guided Radiotherapy," Program Information, AAPM 2017, Jul. 30-Aug. 3.

Van Kranen S, et al. Correction strategies to manage deformations in head-and-neck radiotherapy. Radiother Oncol. 2010;94:199-205.

Van Kranen S, et al. Setup uncertainties of anatomical sub-regions in head-and-neck cancer patients after offline CBCT guidance. Int J Radiat Oncol Biol Phys. 2009;73:1566-1573.

Xia, Wenyao, et al. "Image registration assessment in radiotherapy image guidance based on control chart monitoring." Journal of Medical Imaging 5.2 (2018): 021221.

Yaegashi, Y. et al. "Assessment of Similarity Measures for Accurate Deformable Image Registration," J. Nucl. Med. Radiat. Ther. vol. 3, 4, 2012.

* cited by examiner

SYSTEMS AND METHODS FOR QUALITY CONTROL IN IMAGE-GUIDED RADIOTHERAPY

CROSS-REFERENCE TO RELATED APPLICATIONS

This application claims the benefit of U.S. Provisional Patent Application Ser. No. 62/713,683 filed on Aug. 2, 2018 and entitled "Systems and Methods for Quality Control in Image-Guided Radiotherapy," which is incorporated herein by reference as if set forth in its entirety for all purposes.

BACKGROUND

The present disclosure relates generally to systems and methods for image-guided radiotherapy (IGRT) and, in particular, to systems and methods for quality control in IGRT.

In modern-day radiotherapy, imaging studies are first performed and used to develop a treatment plan. The radiation treatment is then divided into several "fractions", which are delivered over the course of several days or weeks. To ensure consistency between the fractions, most institutions use image guidance for patient localization before each treatment, with volumetric imaging being the most commonly used modality across all treatment sites. Coupled with advances in delivery technology, IGRT has opened up opportunities such as dose-escalation, hypofractionation, and a reduced margin between clinical target volume (CTV) and planning target volume (PTV) by decreasing geometric uncertainties associated with patient setup at each treatment.

While image guidance is a critical part of radiotherapy, current quality control processes used by both therapists and physicians are often subjective. For instance, different reviewers may have different opinions or expectations for alignment accuracy required between the simulation images used for planning and the pre-treatment images. In addition, evaluation of three-dimensional (3-D) image registration is challenging when multiple critical structures are present, or when there is deformation. At most institutions where volumetric localization is the standard of practice, therapists have to review image registrations and make a decision as to whether the alignment is acceptable for treatment, and physicians review the images after the treatment, which complicates achieving inter-reviewer consistency.

Furthermore, because methods to evaluate statistical trends in image registrations over multiple treatment days are not standard practice, achieving inter-fraction consistency is difficult. Also, automatic rigid registration of images may not result in clinically optimal registrations. This is because the accuracy of automatic registration algorithms depends on many variables such as size of the selected volume of interest, registration algorithms, search space, and image qualities. Studies have shown the presence of significant residual setup errors due to deformed anatomy after automatic rigid registrations.

While IGRT has opened up opportunity to precisely deliver highly conformal dose distributions, current IGRT processes do not guarantee an optimal patient setup. Therefore, there is a need for developing objective quality control processes that can ensure accuracy in radiotherapy.

SUMMARY

The present disclosure overcomes the aforementioned drawbacks by providing systems and methods for quality control in image-guided radiotherapy. The foregoing and other advantages of the invention will appear from the following description.

In accordance with one aspect of the disclosure, a method for quality control in image-guided radiotherapy is provided. The method includes accessing treatment images of a subject acquired using an imaging system, with the treatment images including at least one registration tracking volume (RTV). The method also includes generating simulation images of the subject using the imaging system, with the simulation images including the registration tracking volume (RTV). The method also includes performing a registration using the treatment images and simulation images. At least one similarity metric is computed for the at least one RTV based on the registration performed and a conformance is determined of the at least one similarity metric to predetermined limits. A report is generated indicative of the conformance, with the report indicating a quality control for image-guided radiotherapy.

In accordance with another aspect of the disclosure, a system for quality control in image-guided radiotherapy is provided. The system includes a computer system configured to: i) access treatment images of a subject acquired using an imaging system, with the treatment images including at least one registration tracking volume (RTV); ii) generate simulation images of the subject using a treatment planning system, with the simulation images including the registration tracking volume (RTV); iii) perform a registration using the treatment images and simulation images; iv) compute at least one similarity metric for the at least one RTV based on the registration performed; v) determine a conformance of the at least one similarity metric to predetermined limits; and vi) generate a report indicative of the conformance, with the report indicating a quality control in image-guided radiotherapy.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The present invention will hereafter be described with reference to the accompanying drawings, wherein like reference numerals denote like elements. The patent or application file contains at least one drawing executed in color. Copies of this patent or patent application publication with color drawing(s) will be provided by the Office upon request and payment of the necessary fee.

DETAILED DESCRIPTION

Conventional radiotherapy processes rely on subjective evaluations of image registration between simulation images obtained during the treatment planning phase, and images acquired prior to treatment. This can lead to setup errors that can reduce treatment effectiveness, increase radiation exposure of non-targeted structures, and affect patient outcome. To address these problems in the field, the present disclosure introduces an objective quality control approach that can ensure review and treatment consistency, as well as increase the efficiency of the IGRT process. Using a framework that incorporates statistical process control (SPC) and similarity metrics as measures of image registration quality, systems and methods described herein can be used to evaluate and track patient setup.

Systems and methods described herein may be used as on-line tools that can provide clinicians with real-time feedback regarding registration quality, and may provide information regarding outliers that might require action. Such tools may also assist in off-line reviewing processes, allowing objective monitoring of image registration and treatment consistency over the course of a treatment.

Figure 1:
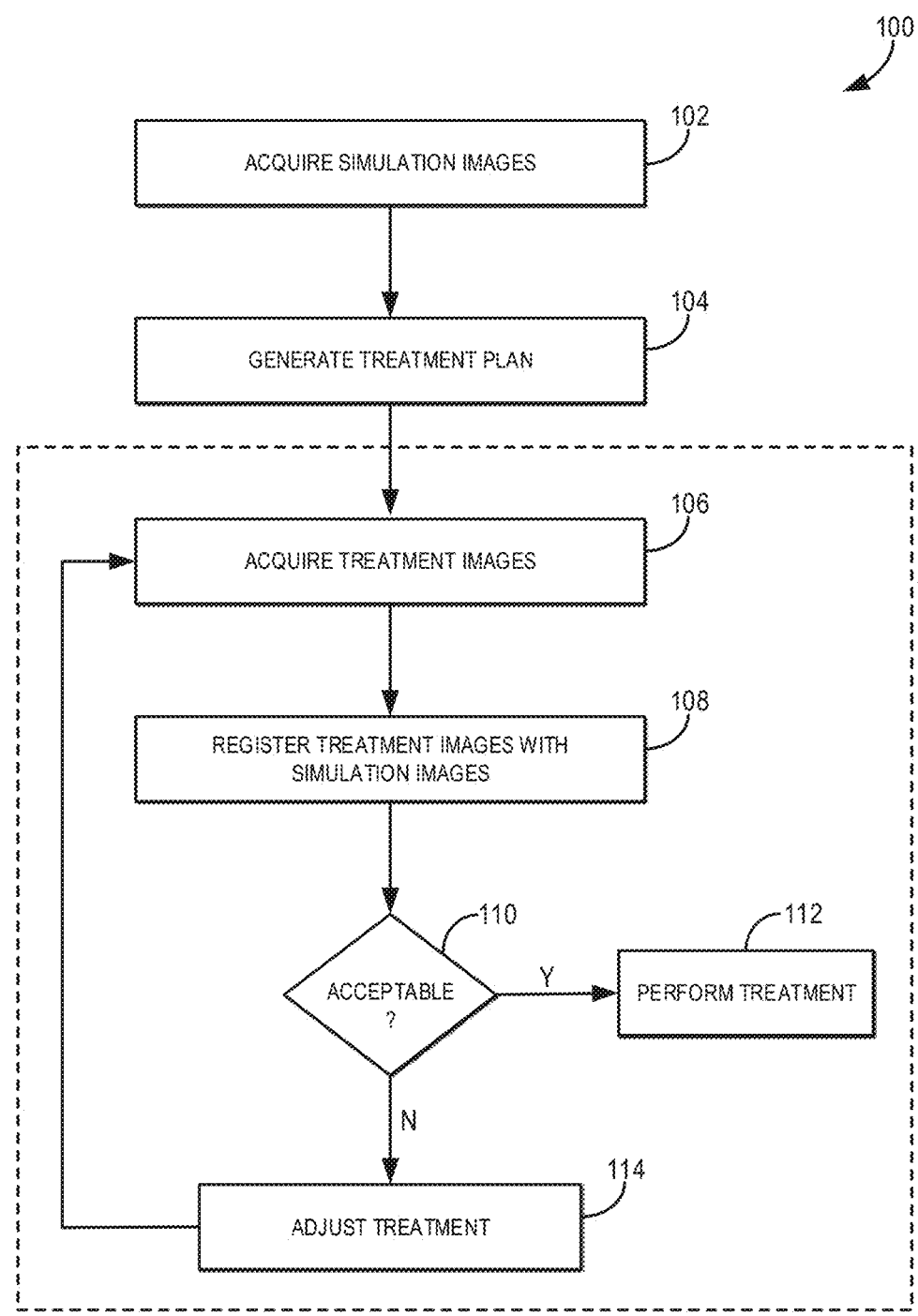
FIG. 1 illustrates steps of a process, in accordance with aspects of the present disclosure.

Referring to FIG. 1, a flowchart setting forth non-limiting example steps of a process 100, in accordance with aspects of the present disclosure, is shown. Steps of the process 100 may be carried out using any suitable device, apparatus or system, such as systems described herein. Steps of the process 100 may be implemented as a program, firmware, software, or instructions that may be stored in non-transitory computer readable media and executed by a general-purpose, programmable computer, processor or computing device. In some implementations, steps of the process 100 may also be hardwired in an application-specific processor or dedicated module.

The process 100 may begin at process block 102 with a simulation process in which simulation images are acquired. Simulation images may be generated by an imaging system and are typically acquired for purposes of treatment planning, such as by transferring the simulated images from the imaging system to a treatment planning system. Simulation images may be acquired as part of a Radiation Oncology workflow. The simulation images may include a combination of computed tomography (CT), magnetic resonance (MR), positron emission tomography (PET), ultrasound (US) images, and others. In some aspects, the simulation images may be retrieved from a storage location or database. Alternatively, the simulation images may be acquired using one or more suitable imaging systems. Using various techniques known in the field, a treatment plan may then be generated at process block 104 based on the simulation images.

Prior to treatment, treatment images may be acquired, as indicated by process block 106. The treatment images are typically used for patient setup and localization. In one non-limiting example, the treatment images include volumetric images, such as cone-beam CT (CBCT) images. Other treatment images may also be acquired at process block 106. The simulation and treatment images may then be registered at process block 108 using various image registration techniques. The registration process helps clinicians determine the adjustments (e.g. couch and/or patient movements) necessary to appropriately position the patient relative to the treatment machine. In some aspects, images may be resampled prior to registration to match the treatment and simulation images. Other pre-processing methods may also be carried out.

As described below, a statistical process control (SPC) framework based on similarity metrics may be used at process block 108 to determine whether image registration is acceptable. A report may then be generated, providing real-time, online feedback to clinicians. In some implementations, the report may include control charts identifying patient-specific trends, and statistical information corresponding to prior treatments of the patient or a population. For example, the control charts may indicate a moving average of one or more similarity metrics and upper/lower limits indicating statistically expected variations of the similarity metric(s) computed for the patient as well as other information. The control charts may also show a conformance of similarity metrics to predetermined limits or averages, and highlight clinically meaningful outliers or deviations from the patient-specific or population-specific limits. The report may also identify critical failure modes and provide recommendations for addressing conditions or events potentially leading to the deviations or critical failures.

Using the provided feedback, an evaluation may then be carried out at decision block 110 to determine whether conditions are suitable for treatment. The evaluation may complement other quality assurance steps, including pre-treatment patient setup verification, physician offline review and evaluation of patient setup, as well as pre-treatment beam path verification in proton therapy.

Should results of the evaluation indicate that treatment can continue, the treatment can be performed at process block 112. If not, the treatment can be adjusted at process block 114, and step 106 repeated, as shown in FIG. 1.

Figure 5:
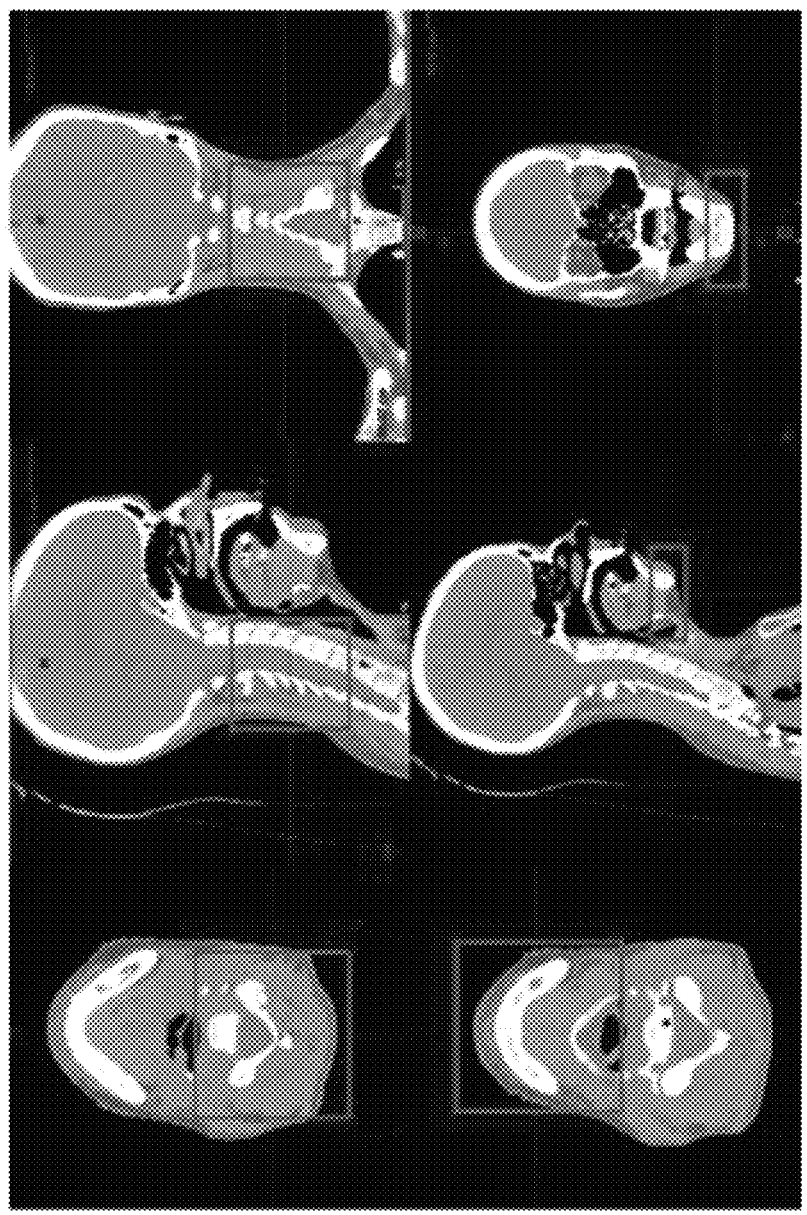
FIG. 5 shows example registration target volumes, in accordance with aspects of the present disclosure.

In one configuration, an SPC framework may rely on one or more similarity metrics calculated for one or more volumes of interest (VOI), or registration tracking volume (RTV), selected in simulation and treatment images. The RTV may be a separate volume of interest from conventional registration volumes used at the time of patient setup. Conventional registration volumes may be based upon large anatomy, such as bony structures. The RTVs may be selected as target volumes, or sub-volumes, where the target volumes correspond to volumes sensitive to radiation treatment. RTVs may be selected to be regions where alignment is especially critical or surrogate for the critical volume such as locations in or near the spine, mandible, and the like. When tracking image registration from multiple fractions, it is advantageous that selection of each RTV remains consistent for each fraction. As a non-limiting example, FIG. 5 shows two selected RTVs, namely a "C-spine" RTV defined by an 8×8×8 $cm^3$ box around the cervical spine (approximately C2-C7), and a "Mandible" RTV, defined by 8×8×3 $cm^3$ around the lower mandible. It may be readily understood that these RTVs are non-limiting examples, and the size, shape and location of the selected RTVs may vary.

Various similarity metrics may be utilized in the present framework, such as mutual information (MI) and normalized cross-correlation (NCC), and others. In particular, MI is defined as:

$$MI = \sum_{a,b} p(a, b) \log \frac{p(a, b)}{p(a)p(b)}, \quad (1)$$

where a and b are pixel values in the RTV selected in registered images, such as the simulation and treatment images described above. In addition, p(a) and p(b) are probabilities of those pixel values in the RTV. The p(a, b) term is the probability of the treatment image having a b pixel value given the simulation image has an a pixel value in the corresponding voxel. The normalized cross-correlation for an RTV of a first image A and a second image B is defined as:

$$NCC = \frac{1}{N} \sum_{\vec{x}} \frac{(A(\vec{x}) - \overline{A})(B(\vec{x}) - \overline{B})}{\sigma_A \sigma_B}, \quad (2)$$

where N is the number of voxels in the RTV, $A(\vec{x})$ is pixel value at $\vec{x}$, and $\overline{A}$ and $\sigma_A$ are the average and standard deviations, respectively, of all pixel values in the RTV corresponding to the first image A. Similarly, $B(\vec{x})$ is pixel value at $\vec{x}$, and $\overline{B}$ and $\sigma_B$ are the average and standard deviations, respectively, of all pixel values in the RTV corresponding to the first image B.

In some aspects, selection of the similarity metric(s) to be used in the present SPC framework may depend on the target site or region being monitored or tracked. For instance, NCC may be better suited for the head and neck region compared to MI.

Similarity metrics, as described above, may be tracked over time or treatment fractions, and provided as feedback to clinicians, for instance, using control charts. In addition to measured data points of the metrics, control charts may also include various other statistical indicators or statistical information, and the like. In one non-limiting example, a center line may be displayed to indicate an average value of the similarity metrics. In another non-limiting example, upper and lower lines or limits reflecting patient and/or population-specific statistical variations may also be displayed. In yet another non-limiting example, a moving average and limits may be computed using a predetermined number of previous data points (e.g. data from the previous 5 fractions), and displayed.

Statistical information reflected in a patient-specific control chart may be computed using baseline data. For example, similarity metrics computed for the first five fractions of a treatment of a patient may be used as baseline data to calculate the average similarity metric, $\bar{x}$. In addition, the upper limit (UL) and lower limit (LL) may be computed using: $UL=\bar{x}+3\hat{\sigma}$ and $LL=\bar{x}-3\hat{\sigma}$, where $\hat{\sigma}$ is the estimator of the true standard deviation. The relationship between the sample range R and the standard deviation $\sigma$ may be described by the relative range, $W=R/\sigma$, which is tabulated $W=1.128\pm0.853$ for a sample size of two. Therefore, the estimated of the true standard deviation may then be estimated based on the mean of the relative range, as $\hat{\sigma}=\overline{R}/1.128$. In some aspects, the variable $\overline{R}$ may be obtained using the average of the first four range measurements, $R_2$ through $R_4$, where $R_i=|x_i-x_{i-1}|$, with $x_i$ being the similarity metric for the $i^{th}$ fraction.

Figure 2:
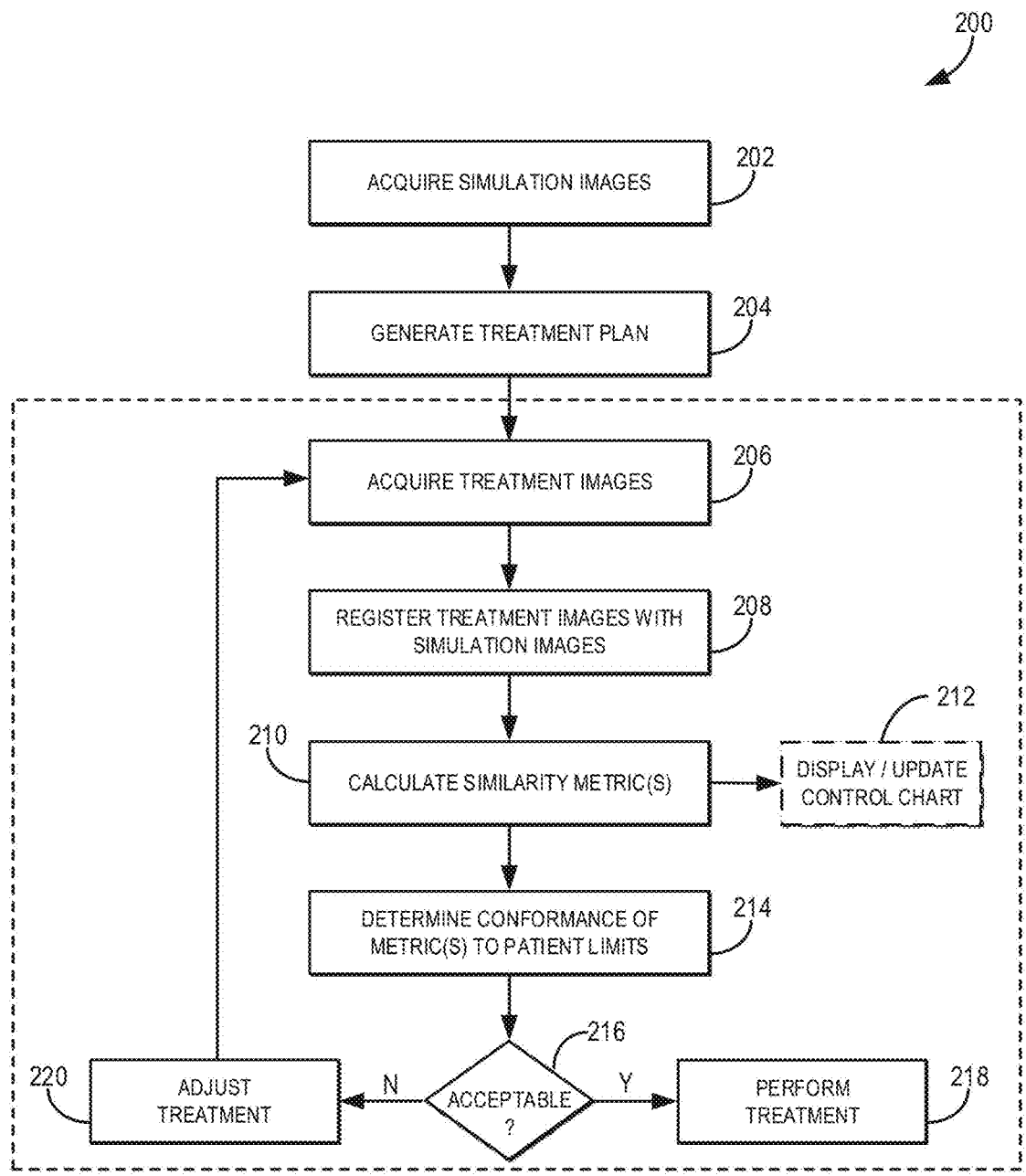
FIG. 2 illustrates steps of another process, in accordance with aspects of the present disclosure.

Turning now to FIG. 2, a flowchart setting forth steps of another process 200, in accordance with aspects of the present disclosure, is shown. Steps of the process 200 may be carried out using systems described herein, as well as other suitable devices. Steps of the process 200 may also be implemented as a program, firmware, software, or instructions stored in non-transitory computer readable media that may be executed by a general-purpose computer, application-specific processor or dedicated module.

Similar to process 100 in FIG. 1, the process 200 may also include steps of acquiring simulation images, generating a treatment plan, acquiring treatment images and registering the treatment images with the simulation images, as indicated by process blocks 202-208, respectively.

Then at process block 210 one or more similarity metrics may be computed based on the registration performed at process block 208. As described above, the similarity metrics may be computed using one or more selected RTVs in corresponding images. In some aspects, a report may be generated and provided as feedback to clinicians. In one non-limiting example, the report may include a patient-specific control chart that is displayed and/or updated, as indicated by process block 212. As described above, patient-specific limits may be determined at process block 212 based on baseline data obtained from prior fractions, such as the previous 5 fractions. In one non-limiting example, patient-specific limits may be computed using the average $\bar{x}$ and standard deviation $\sigma$ computed using the baseline data. The calculated similarity metrics may also be used to determine various clinically-relevant thresholds that might require investigating the cause and suspending or adapting treatment.

Figure 6:
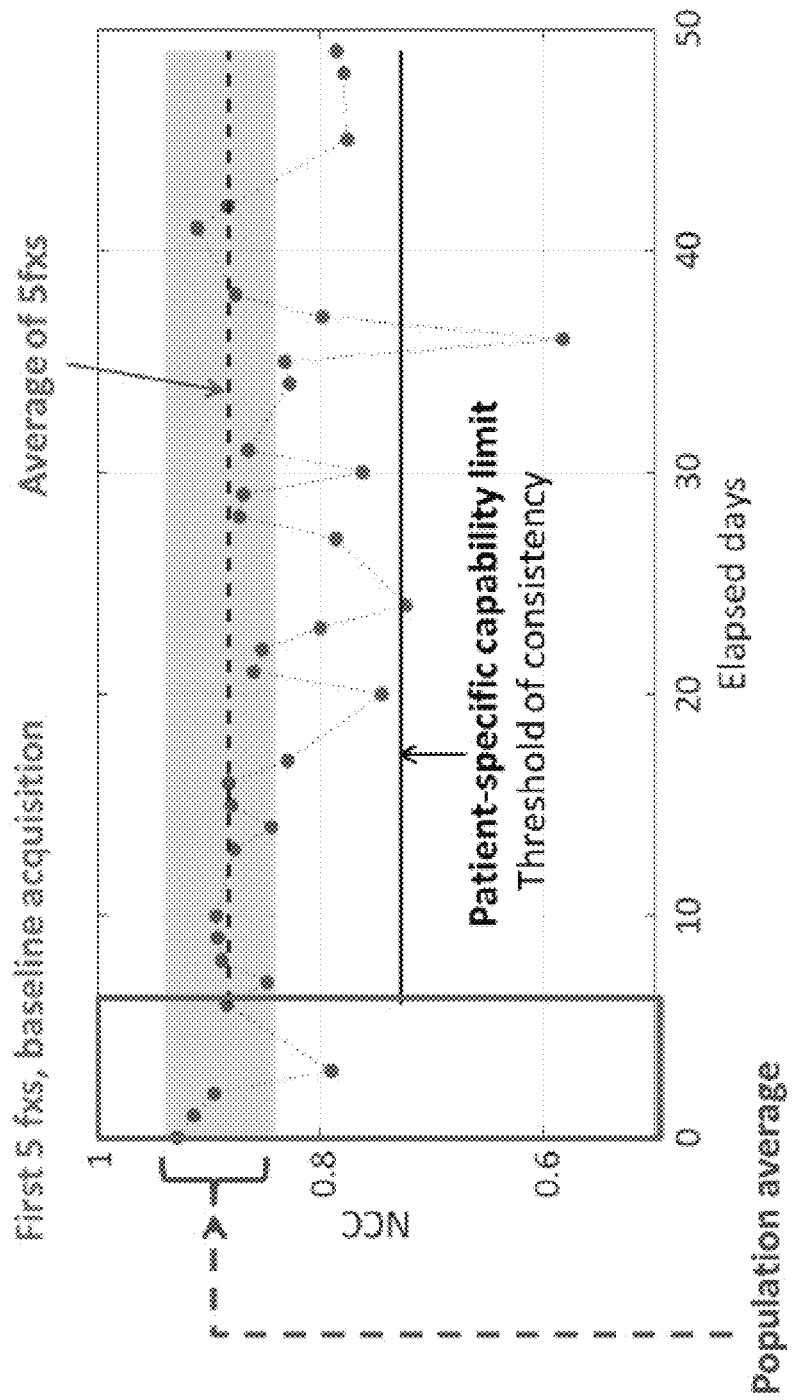
FIG. 6 is a graphical illustration showing an example of a control chart and feedback, in accordance with aspects of the present disclosure.
Figure 7:
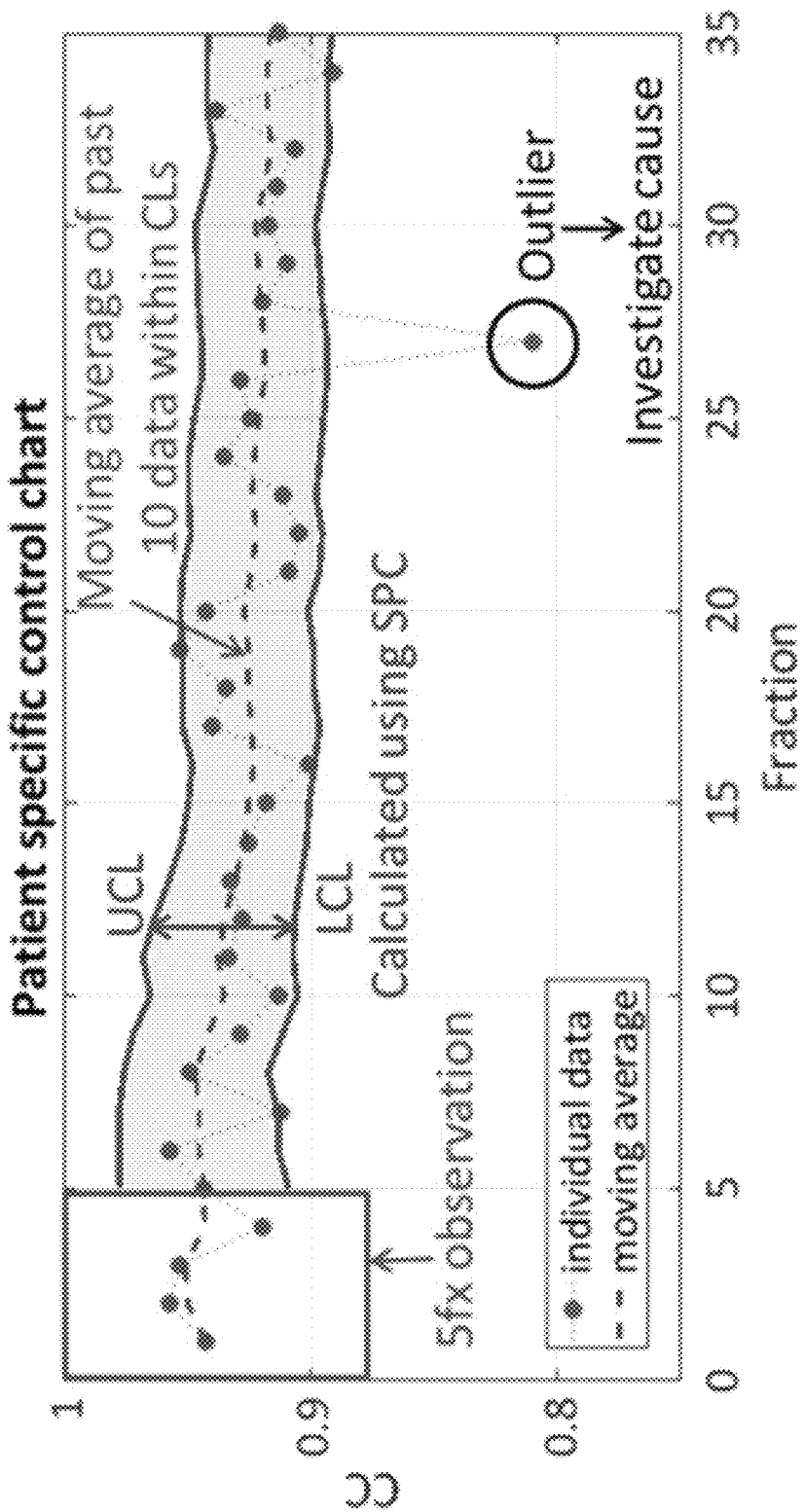
FIG. 7 is a graphical illustration showing another example of a control chart and feedback, in accordance with aspects of the present disclosure.
Figure 8:
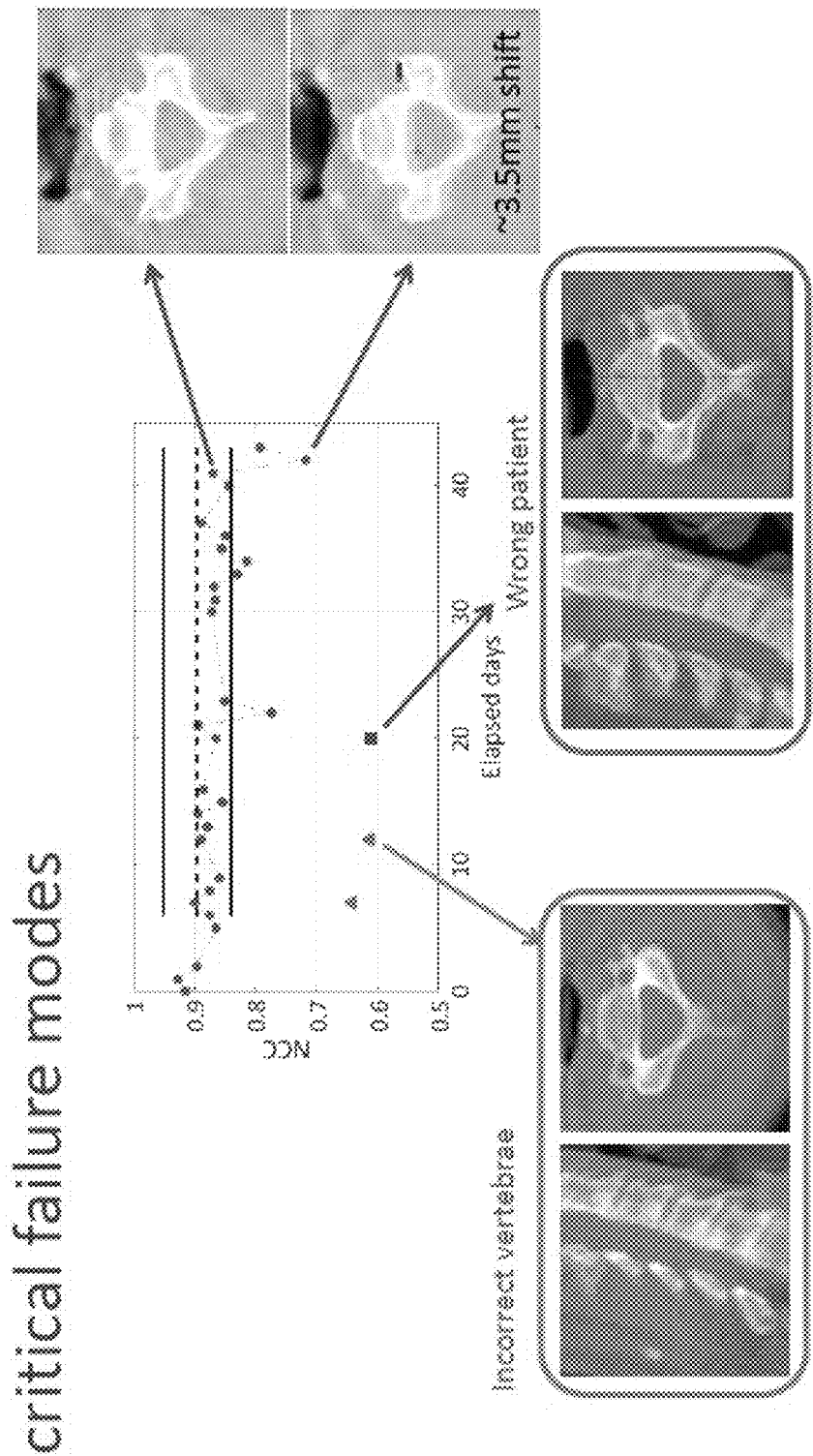
FIG. 8 is a graphical illustration showing yet another example of a control chart and feedback, in accordance with aspects of the present disclosure.

A conformance of the metric(s) to patient-specific limits may then be determined, as indicated by process block 212. In some aspects, outliers or other metric deviations, along with other information or feedback may be highlighted in the displayed control chart. As examples, FIGS. 6-8 illustrate various information that may be provided to clinicians along with control charts.

An evaluation performed at decision block 216 may use results from the determination at process block 214, as well as other information, to identify whether treatment conditions are acceptable. If treatment conditions are acceptable, the treatment is performed at process block 218. If treatment plans are not acceptable, treatment may be adjusted at process block 220 and the process 200 repeated by acquiring new treatment images at process block 206 after adjustments are made.

Since similarity metrics can depend on pixel value distributions in the RTV, and each patient can have anatomical landmarks of slightly different shape and size, similarity metric values may be patient-specific. In some configurations, however, if variability among patient anatomy is less than variability originating from image misalignment, a population analysis can help identify patients whose setup reproducibility is very different from that of other patients.

Furthermore, there is a category of therapy called Stereotactic Body Radiotherapy (SBRT), which lasts for 5 or fewer treatments. The nature of SBRT treatment is such that much higher radiation doses (5-10 times higher than conventional radiotherapy) are delivered on each treatment day. For these patients, setup and localization reproducibility is especially critical for the success of the treatment. Without information from other treated patients, it would be difficult to quantitatively evaluate patient setup since SBRT patients complete treatment in 5 days or less. As such, there would not be enough patient-specific data to accurately establish patient-specific limits and evaluate setup consistency throughout treatment.

In some configurations, a population control chart can help identify patients whose setup reproducibility is significantly different from that of other patients. Potential non-limiting example causes, such as unstable immobilization devices or weight loss/swelling of the patient, could cause less reproducible setups. In some aspects, average control charts reflecting the average similarity metric values across multiple patients may be generated. In other aspects, sigma control charts reflecting the variation in the metric across patients may also be generated.

In one non-limiting example, metrics computed over the first five fractions of a treatment may be used to create a population control chart. A center line for an average control chart may be calculated using $$\bar{\bar{X}} = \frac{1}{m}\sum_{j=1}^{j=m} \bar{X}_j,$$

where $\bar{X}_j$ is the average of the first five measurements for the $j^{th}$ patient. Similar to the patient-specific control chart, in one non-limiting example the upper and lower limits may be set at three standard deviations as $UL=\bar{\bar{X}}+3\hat{\sigma}/\sqrt{n}$ and $LL=\bar{\bar{X}}-3\hat{\sigma}/\sqrt{n}$, where $\hat{\sigma}/\sqrt{n}$ is the estimator of the standard deviation of the means. In the average control chart, $\hat{\sigma}$ may be calculated using $\hat{\sigma}=\bar{S}/c_4$ where $$\bar{S} = \frac{1}{m}\sum_{j=1}^{j=m} S_j$$

and $S_j$ is the standard deviation for the first five fractions for the $j^{th}$ patient. For a normal distribution for a sample size of five, the constant $c_4$ is tabulated at $c_4=0.940$.

Similarly, a sigma control chart may be created with the center line at an $\bar{S}$, with upper and lower limits according to $UL=\bar{S}+3\hat{\sigma}\sqrt{1-c_4^2}$ and $LL=\bar{S}+3\hat{\sigma}\sqrt{1-c_4^2}$, where $\hat{\sigma}\sqrt{1-c_4^2}$ is the estimator of the standard deviation of S.

In one configuration, similarity metric values may be related to spatial displacement, which may make interpretation of the metric more intuitive for users and may allow an action limit to be set based on spatial displacements. Since similarity metrics may be scalar values and have no directional information, assumptions about the direction of displacement may be made to relate the values to spatial distances. In one non-limiting example, a similarity metric may be related to a spatial displacement by assuming a directional misalignment, referring to as an effective displacement. In some aspects, patient-specific sensitivity curves may be used to convert metric values to effective displacements.

Figure 3:
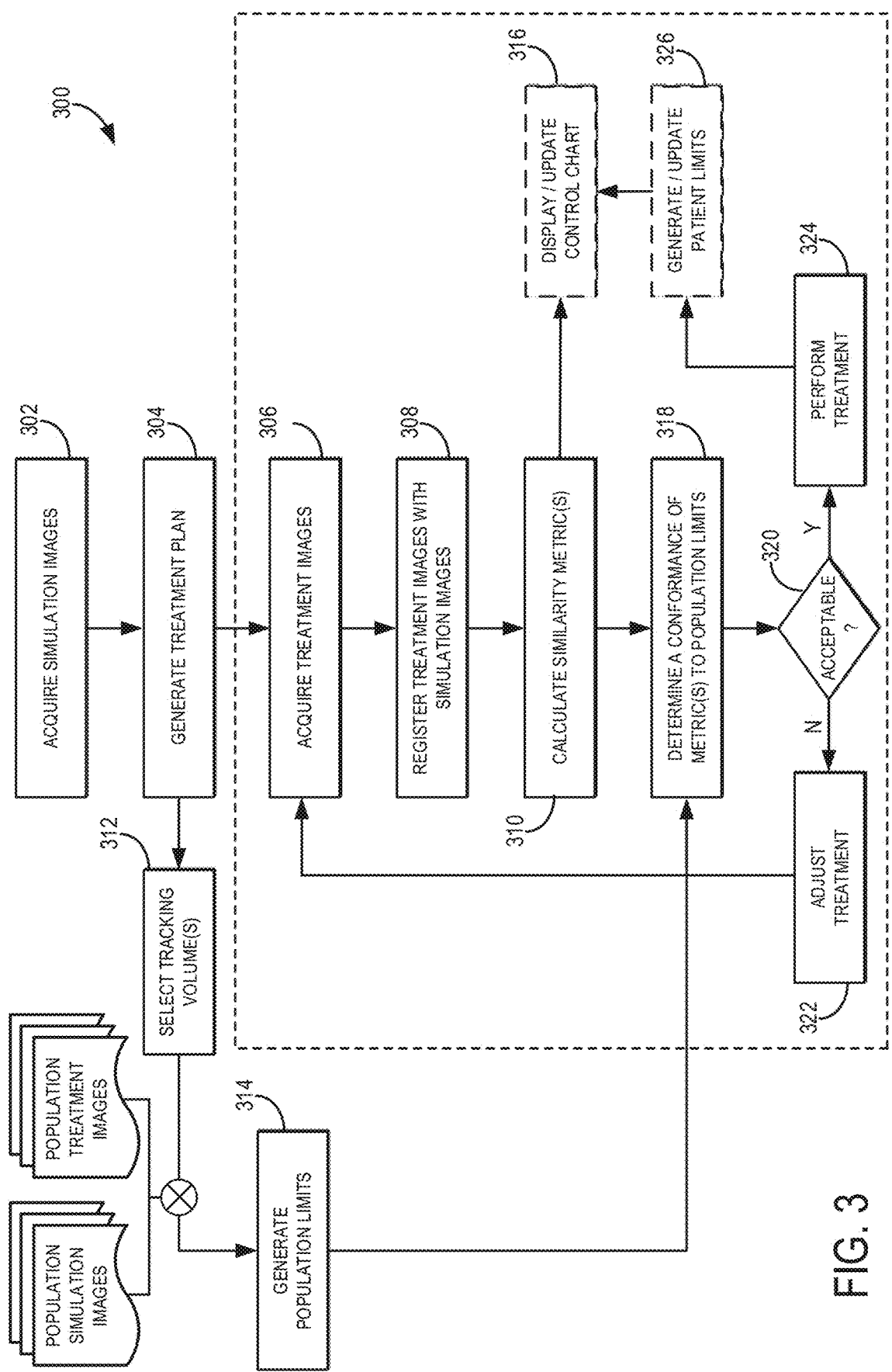
FIG. 3 illustrates steps of yet a process, in accordance with aspects of the present disclosure.

Turning now to FIG. 3, a flowchart setting forth steps of another non-limiting example process 300, in accordance with aspects of the present disclosure, is shown. Steps of the process 300 may be carried out using systems described herein, as well as other suitable devices. Steps of the process 300 may also be implemented as a program, firmware, software, or instructions stored in non-transitory computer readable media that may be executed by a general-purpose computer, application-specific processor or dedicated module, and the like.

Similar to processes 100 and 200, simulation images may be acquired and a treatment plan generated at process blocks 302 and 304 respectively. Following the acquisition of treatment images at process block 306, a registration process may then be carried out at process block 308 to register the treatment and simulation images. Based on the registration, one or more similarity metric(s) may be calculated at process block 310. The similarity metrics may be calculated using the same registration tracking volumes selected, as indicated by process block 312. In some aspects, control charts may be optionally displayed and/or updated, as indicated by process block 316.

As shown in FIG. 3, population images and data may be acquired, and used to generate population limits, as well as other statistical information, at process block 314. The population limits may be used at process block 318 to determine a conformance of the computed similarity metric(s) to the population obtained using population baseline data. Based on the determination at process block 318, an evaluation is made at decision block 320 whether treatment conditions are acceptable. If treatment conditions are acceptable, the treatment is performed at process block 324. If treatment conditions are not acceptable, treatment may be adjusted at process block 322 and the process 300 repeated by acquiring new treatment images process block 3026 after adjustments are made.

In some aspects, patient limits may be generated and/or updated, as indicated by process block 326. For instance, if sufficient baseline data is obtained (for example, from 5 treatment fractions), patient-specific limits may be computed, as described. Furthermore, such patient-specific limits may also be indicated in an updated or displayed control chart, as shown by process block 316.

In some implementations, the present framework can be used to assist physicians during an offline review. Currently, offline review platforms and clinical workflows limit clinicians to reviewing one registration at a time. This makes it very difficult to track registration consistency over the course of a treatment. By contrast, control charts, in accordance with the present disclosure, can provide tracking capability, ensuring that treatment consistency can be accurately analyzed. In some configurations, if a gradual change in patient anatomy or registration consistency is observed, a physician can adapt treatment processes to ensure that volumes targeted for treatment receive the desired radiation dose, while non-target volumes are not unnecessarily irradiated.

Figure 4:
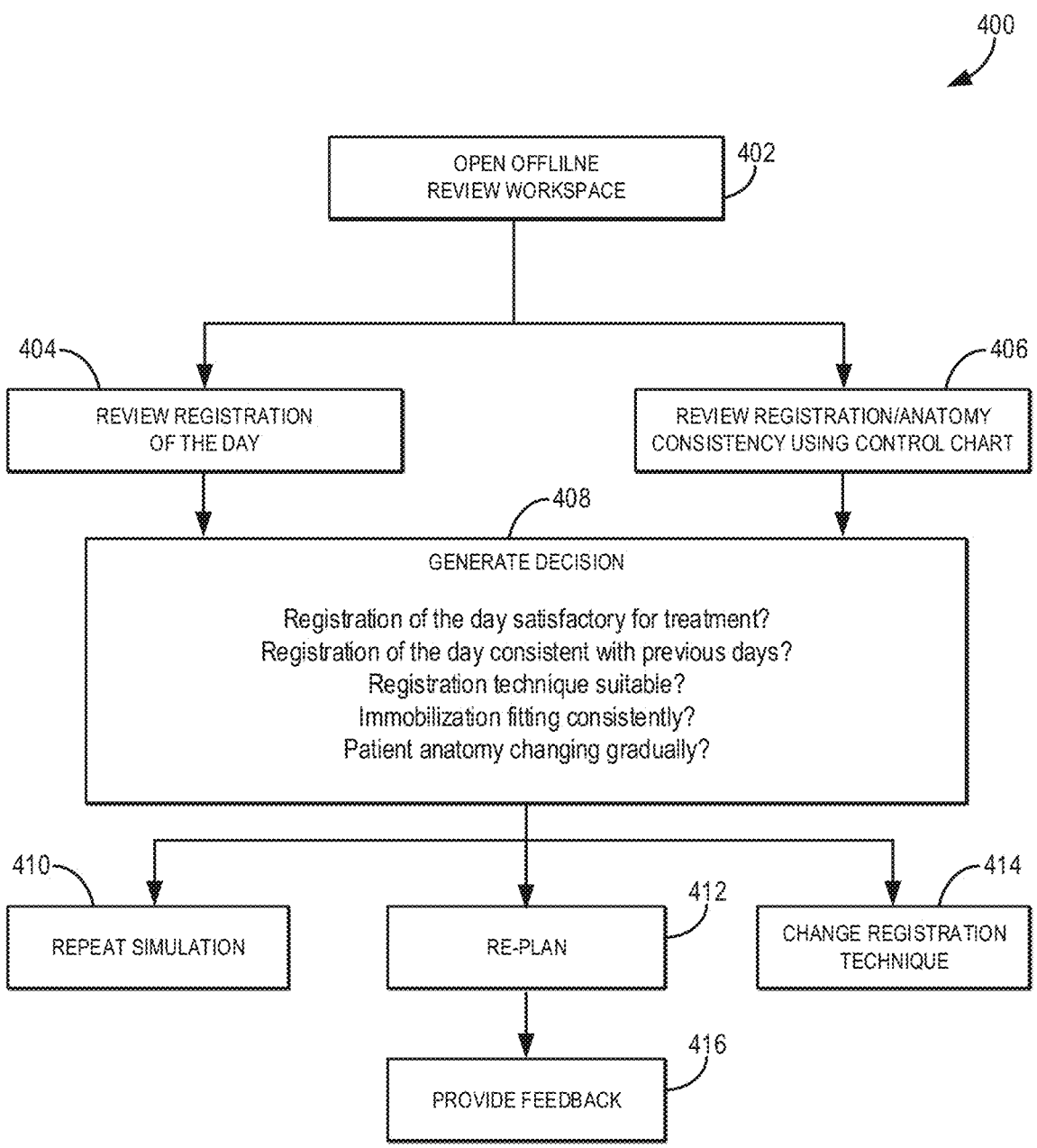
FIG. 4 illustrates steps of a process, in accordance with aspects of the present disclosure.

Referring specifically to the non-limiting example process 400 in FIG. 4, an offline review workspace implementing the present framework may be opened at process block 402. After each delivered fraction, registered simulation and treatment images may be reviewed by a physician as indicated by process block 404. In accordance with methods described herein, registration and anatomy consistency may be reviewed using patient-specific and/or population-specific control charts, as indicated by process block 406.

A decision based on the review may then be generated at process block 408, as shown. It may be appreciated that such decision may be generated with or without clinician input. In some configurations, a programmed processor or module may automatically or semi-automatically conduct an analysis of information generated during the review steps described above. In a non-limiting example, individual values or trends in similarity metrics relative to patient or population-specific limits or thresholds may be used to answer clinically relevant questions. These may include identifying a consistency of registration, identifying changes in anatomy, identifying changes in immobilization, determining a suitability of utilized registration technique, and so on. Based on the generated decision, a simulation or registration may be repeated at process block 410. Alternatively, a re-planning process may be performed, as indicated by process block 410. Alternatively still, a new registration technique may be implemented, as indicated by process block 414. A combination of these may be also be possible. Feedback may then be provided to clinicians, as indicated by process block 416.

Figure 9:
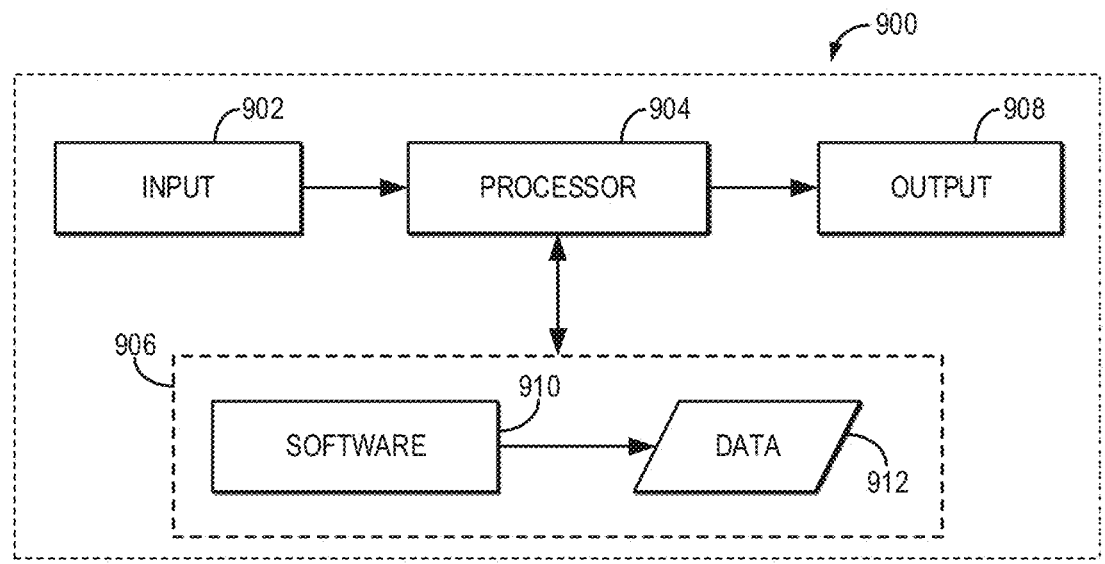
FIG. 9 is a schematic diagram of a system, in accordance with aspects of the present disclosure.

Referring now to FIG. 9, a block diagram of a non-limiting example of a computer system 900 that can perform the methods described in the present disclosure is shown. The computer system 900 generally includes an input 902, at least one hardware processor 904, a memory 906, and an output 908. Thus, the computer system 900 is generally implemented with a hardware processor 904 and a memory 906.

In some configurations, the computer system 900 can be a radiation treatment planning system ("TPS"). The computer system 900 may also be implemented, in some examples, by a workstation, a notebook computer, a tablet device, a mobile device, a multimedia device, a network server, a mainframe, one or more controllers, one or more microcontrollers, or any other general-purpose or application-specific computing device.

The computer system 900 may operate autonomously or semi-autonomously, or may read executable software instructions from the memory 906 or a computer-readable medium (e.g., a hard drive, a CD-ROM, flash memory), or may receive instructions via the input 902 from a user, or any other source logically connected to a computer or device, such as another networked computer or server. Thus, in some embodiments, the computer system 900 can also include any suitable device for reading computer-readable storage media.

In general, the computer system 900 is programmed or otherwise configured to implement the methods and algorithms described in the present disclosure. In some configurations, the computer system 900 may be programmed to apply various registration techniques to register treatment and simulation images. Based on predetermined or user-selected RTVs, the computer system 900 may calculate various similarity metrics and generate feedback, for instance, in the form of control charts, as described. The computer system 900 may also identify a conformance of the calculated metrics to patient and/or population-specific limits.

The input 902 may take any suitable shape or form, as desired, for operation of the computer system 900, including the ability for selecting, entering, or otherwise specifying parameters consistent with performing tasks, processing data, or operating the computer system 900. In some aspects, the input 902 may be configured to receive data, such as data acquired with a medical imaging system, previously generated radiation treatment plans, and so on. Such data may be processed in accordance with methods described herein.

In some configurations, the input 902 may also be configured to receive any other data or information considered useful for implementing the methods described above. Also, among the processing tasks for operating the computer system 900, the one or more hardware processors 904 or processing modules may also be configured to carry out any number of post-processing steps on data received by way of the input 902.

The memory 906 may contain software 910 and data 912, such as data acquired with a medical image system or previously generated radiation treatment plans, and may be configured for storage and retrieval of processed information, instructions, and data to be processed by the one or more hardware processors 904. In some aspects, the software 910 may contain instructions directed to implementing the methods described above.

The output 908 may take any shape or form, as desired, and may be configured for displaying medical images, radiation treatment plans, and other data computed, derived, or otherwise obtained from such images or plans, in addition to other desired information.

Figure 10:
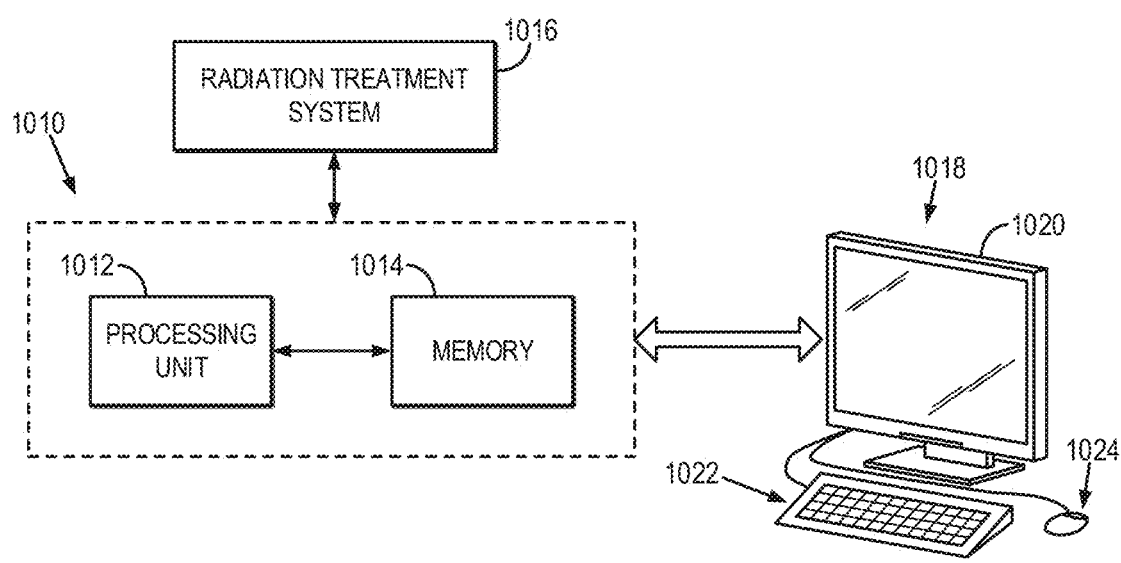
FIG. 10 is a schematic diagram of another system, in accordance with aspects of the present disclosure.

As noted, the systems and methods described in the present disclosure can be implemented in cooperation or may be implemented using a radiation treatment planning system or offline workstation. Referring now to FIG. 10, an example of such a radiation treatment planning system 1010 is illustrated. The radiation treatment planning system 1010 may be in communication with one or more radiation treatment systems 1012, which may include any suitable radiation treatment system.

The radiation treatment planning system 1010 generally includes a memory 1014 that is operably coupled to a processor unit 1016 or processing module. As an example, the processor unit 1016 can be a commercially available computer processor, or an application-specific module as described above. The processor unit 1016 is configured to carry out one or more of the steps of the methods described above.

As non-limiting examples, the memory 1014 can include a plurality of memory elements, or can include a single memory element. In general, the memory 1014 is configured to store information regarding patient data, treatment targets (e.g., a tumors located within a patient), imaging beam model data, treatment beam model data, dose matrices, images, and the like.

The radiation treatment planning system 1010 may include, or may otherwise be in communication with, a user interface 1018. As a non-limiting example, the user interface 1018 provides information to a user, such as a medical physicist. For example, the user interface 1018 can include a display 1020 and one or more input devices, such as a keyboard 1022 and mouse 1024.

In some configurations, any suitable computer readable media can be used for storing instructions for performing the functions and/or processes described herein. For example, in some embodiments, computer readable media can be transitory or non-transitory. In non-limiting examples, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 11:
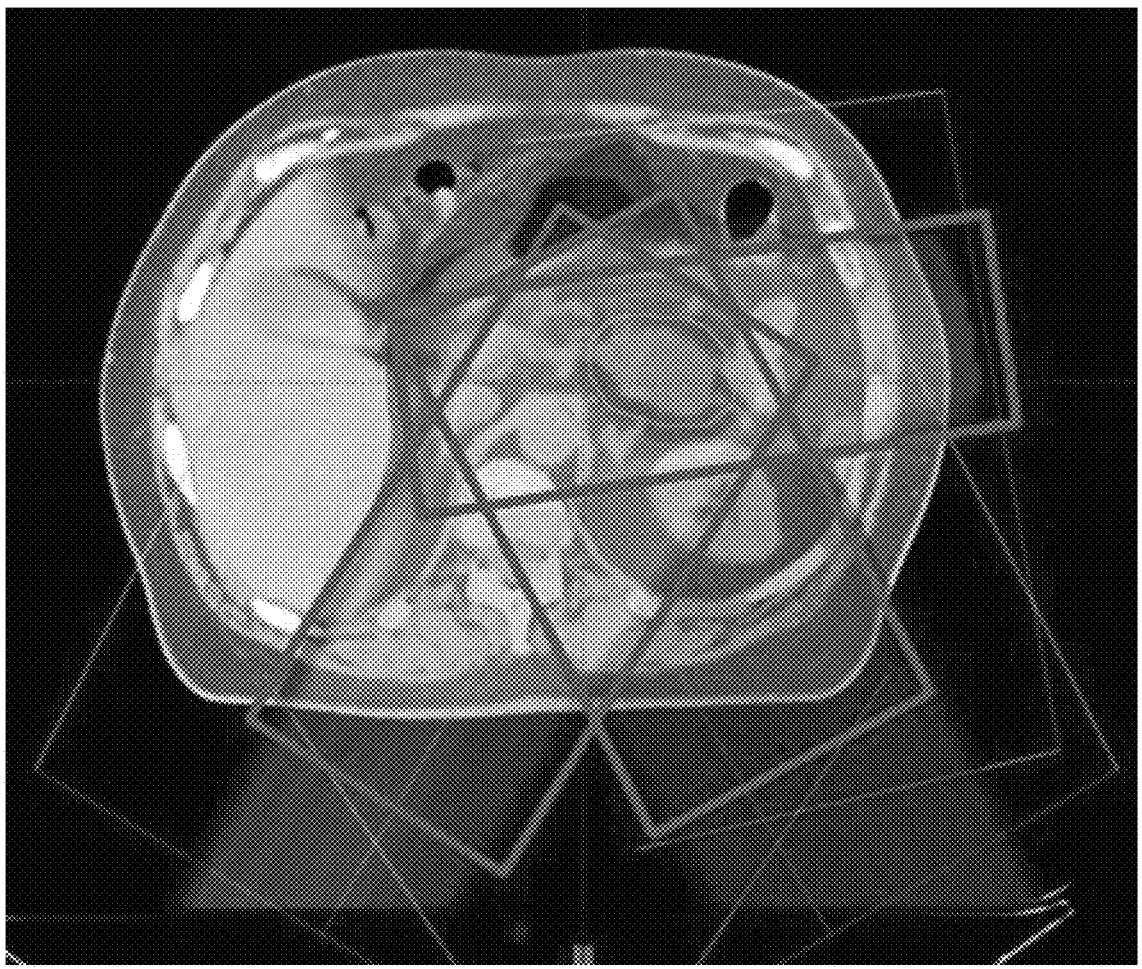
FIG. 11 is an image showing example target volumes corresponding to proton beam paths, in accordance with aspects of the present disclosure.

In one non-limiting example, in addition to tracking target registrations in IGRT, the present framework can also be employed with respect to proton beam therapy. For proton therapy, the path of the proton beam to the treatment target is very important. If the density and amount of tissues that a proton beam passes through varies during the course of treatment, radiation dose may be delivered to unintended volumes. As such, the present approach may be used to track proton beam path to identify consistency in proton treatment. Using selected tracking volumes, as discussed above, similarity metrics may be used to quantify proton beam consistency. By comparing similarity metrics computed using simulation and treatment images, a consistency can be evaluated, as described. As a non-limiting example, FIG. 11 illustrates possible RTVs for proton therapy.

Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A method for quality control in image-guided radiotherapy for multiple fractions of a radiation treatment, the method comprising:
    accessing treatment images of a subject acquired using an imaging system for each fraction of the multiple fractions of the radiation treatment of the subject, wherein the treatment images include at least one registration tracking volume (RTV);
    generating simulation images of the subject using the imaging system, wherein the simulation images include the at least one registration tracking volume (RTV);
    performing a registration using the treatment images and simulation images;
    computing at least one similarity metric for the at least one RTV based on the registration performed;
    generating predetermined limits using similarity metrics computed using similarity metric baseline data acquired from a population, wherein the predetermined limits are determined relative to a statistical measure of the similarity metric baseline data;
    determining a conformance of the at least one similarity metric to the predetermined limits; and
    generating a report indicative of the conformance, wherein the report indicates a quality control between each fraction of the multiple fractions of the radiation treatment of the subject for image-guided radiotherapy.

2. The method of claim 1, wherein the similarity metric includes at least one of mutual information (MI) or normalized cross-correlation (NCC).

3. The method of claim 1, wherein the treatment images comprise at least one of cone beam computed tomography (CBCT) images, or volumetric images.

4. The method of claim 1, wherein the method further comprises selecting the at least one RTV to be a critical volume sensitive to radiation treatment.

5. The method of claim 4, wherein the at least one RTV corresponds to a proton beam path.

6. The method of claim 1, wherein generating the report further comprises displaying the at least one similarity metric on a control chart.

7. The method of claim 6, wherein the method further comprises displaying an average, or the predetermined limits, or both, on the control chart.

8. The method of claim 1, wherein the method further comprises generating the predetermined limits using similarity metrics computed using baseline data acquired from the subject.

9. The method of claim 1, wherein the method further comprises providing a recommendation for treatment based on the conformance.

10. The method of claim 1, wherein the method further comprises adapting a treatment based on the conformance.

11. The method of claim 1, wherein the method further comprises updating the predetermined limits using the at least one similarity metric computed.

12. The method of claim 1, further comprising using the similarity metric baseline data acquired from the population to determine a subject treatment setup.

13. The method of claim 1, wherein the statistical measure of the similarity metric baseline data comprises a center line of an average control chart generated from the similarity metric baseline data.

14. The method of claim 13, wherein the predetermined limits comprise upper and lower limits determined as a number of standard deviations from the centerline of the average control chart.

15. The method of claim 1, wherein the statistical measure of the similarity metric baseline data comprises a center line of a sigma control chart generated from the similarity metric baseline data.

16. The method of claim 15, wherein the predetermined limits comprise upper and lower limits determined as a number of standard deviations from the centerline of the sigma control chart.

17. A system for quality control in image-guided radiotherapy for multiple fractions of a radiation treatment, the system comprising:
    a computer system configured to:
        i) access treatment images of a subject acquired using an imaging system for each fraction of the multiple fractions of the radiation treatment of the subject, wherein the treatment images include at least one registration tracking volume (RTV);
        ii) generate simulation images of the subject using the imaging system, wherein the simulation images include the at least one registration tracking volume (RTV);
        iii) perform a registration using the treatment images and simulation images;
        iv) compute at least one similarity metric for the at least one RTV based on the registration performed;
        v) generate predetermined limits using similarity metrics computed using similarity metric baseline data acquired from a population, wherein the predetermined limits are determined relative to a statistical measure of the similarity metric baseline data;
        vi) determine a conformance of the at least one similarity metric to the predetermined limits; and
        vii) generate a report indicative of the conformance, wherein the report indicates a quality control between each fraction of the multiple fractions of the radiation treatment of the subject in image-guided radiotherapy.

18. The system of claim 17, wherein the similarity metric includes at least one of mutual information (MI) or normalized cross-correlation (NCC).

19. The system of claim 17, wherein the treatment images comprise at least one of cone beam computed tomography (CBCT) images, or volumetric images.

20. The system of claim 17, wherein the computer system is further configured to select the at least one RTV to be a critical volume sensitive to radiation treatment.

21. The system of claim 20, wherein the at least one RTV corresponds to a proton beam path.

22. The system of claim 17, wherein generating the report further comprises displaying the at least one similarity metric on a control chart.

23. The system of claim 22, wherein the computer system is further configured to display an average, or the predetermined limits, or both, on the control chart.

24. The system of claim 17, wherein the computer system is further configured to generate the predetermined limits using similarity metrics computed using baseline data acquired from the subject.

25. The system of claim 17, wherein the baseline data comprises data acquired over five fractions or fewer of a radiotherapy treatment.

26. The system of claim 25, wherein the radiotherapy treatment is a stereotactic body radiation therapy (SBRT).

27. The system of claim 17, wherein the computer system is further configured to provide a recommendation for treatment based on the conformance.

28. The system of claim 17, wherein the computer system is further configured to adapt a treatment based on the conformance.

29. The system of claim 17, wherein the computer system is further configured to update the predetermined limits using the at least one similarity metric computed.

30. The system of claim 17, wherein the computer system is further configured to use the similarity metric baseline data acquired from the population to determine a subject treatment setup.

31. The system of claim 17, wherein the statistical measure of the similarity metric baseline data comprises a center line of an average control chart generated from the similarity metric baseline data.

32. The system of claim 31, wherein the predetermined limits comprise upper and lower limits determined as a number of standard deviations from the centerline of the average control chart.

33. The system of claim 17, wherein the statistical measure of the similarity metric baseline data comprises a center line of a sigma control chart generated from the similarity metric baseline data.

34. The system of claim 33, wherein the predetermined limits comprise upper and lower limits determined as a number of standard deviations from the centerline of the sigma control chart.

* * * * *